United States Patent [19]

Okuda et al.

[11] 4,451,235
[45] May 29, 1984

[54] PROCESS FOR PREPARING AN ARTIFICIAL DENTAL ROOT

[75] Inventors: Kensuke Okuda, Tokorozawa; Hirosi Nagai, Chofu; Hiroto Fujimaki, Kokubunji; Atsushi Tomonaga, Tachikawa; Hideki Aoki, Funabashi, all of Japan

[73] Assignee: Kureha Kagaku Kogyo Kabushiki Kaisha, Tokyo, Japan

[21] Appl. No.: 481,886

[22] Filed: Apr. 4, 1983

Related U.S. Application Data

[63] Continuation of Ser. No. 240,100, Mar. 3, 1981, abandoned, which is a continuation of Ser. No. 78,202, Sep. 24, 1979, abandoned.

[30] Foreign Application Priority Data

Oct. 8, 1978 [JP] Japan ................................. 53-123571

[51] Int. Cl.$^3$ ................................................. A61K 6/08
[52] U.S. Cl. ...................................... 433/201; 106/35; 260/998.11; 433/202; 433/212; 433/215; 523/115
[58] Field of Search .................... 106/35; 260/998.11; 433/201, 228, 202, 212, 215; 523/115

[56] References Cited

U.S. PATENT DOCUMENTS 4,097,935  7/1978  Jarcho ..................................... 3/1.9

Primary Examiner—Lorenzo B. Hayes
Attorney, Agent, or Firm—Murray, Whisenhunt and Ferguson

[57] ABSTRACT

An artificial dental root comprised of a particulate or powdered form of synthetic hydroxyapatite or calcined or sintered synthetic hydroxyapatite or a mixture thereof and an organic matrix, the surface area of said artificial dental root to be brought into contact with a bone being composed of both a phase of said hydroxyapatite and a phase of said organic matrix. The artificial dental root is prepared by blending said hydroxyapatite with said organic matrix and molding the blend. The artificial dental root has moderate affinity for a bone and high mechanical strength.

4 Claims, No Drawings

PROCESS FOR PREPARING AN ARTIFICIAL DENTAL ROOT

This is a Continuation application of Ser. No. 240,100, filed Mar. 3, 1981, now abandoned, which is a continuation of Ser. No. 78,202, filed Sept. 24, 1979, now abandoned.

BACKGROUND OF THE INVENTION

(1) Field of the Invention

The invention relates to an artificial dental root comprised of synthetic hydroxyapatite or calcined or sintered synthetic hydroxyapatite or a mixture thereof (hereinafter, referred to as hydroxyapatite) and an organic matrix. More particularly, the invention relates to an artificial dental root obtained by blending hydroxyapatite with an organic polymerizable binder or organic binding polymeric material (hereinafter, referred to as an organic matrix) and molding the blend.

(2) Description of Prior Art

Artificial dentures include artificial tooth crowns and dens succedaneuses for the prosthesis of respective damaged tooth crowns as well as bridgework for the prosthesis in the case where one or more teeth are lost. The bridgework technique utilizes an artificial denture provided with one or two bridges for supporting it to the normal tooth or teeth. However, the bridgework technique has a drawback in that, since the bridgework is placed on the oral mucosa merely supported by the bridges, it has insufficient retention-ability and, thus, is greatly inferior in the performance of mastication as compared to a natural tooth. This technique has another drawback in that the natural tooth used for support is hurt. Therefore, in order to eliminate the drawbacks, implant dentures have recently been developed, in which the lower construction of a denture is implanted into a vital tissue within the jaw bone, under the periosteum or within the mucous membrane to form an abutment, i.e. an artificial dental root, and the upper structure of the denture is connected to the abutment.

As the materials for such artificial dental roots, there have hitherto been utilized metallic substances such as cobalt-chrome alloy, titanium and tantalum, ceramic materials such as porous alumina ceramics, as well as glass-like carbon and a composite material consisting of polymethyl methacrylate and bone minerals incorporated into the polymethyl methacrylate. However, these materials have drawbacks with respect to toxicity to vital tissue, affinity for a bone, impediment to a bone formation, durability, mechanical strength and the like and, thus, may not provide satisfactory results.

On the other hand, recently, bioceramics based on apatite substances have increasingly become of great interest, as they may be absorbed into body and replaced by a new bone which is a host and, thus, exhibit good affinity for vital tissue. However, the apatite substances have a drawback in that they are inferior in mechanical strength, particularly in impact resistance. Accordingly, studies for the utilization of the apatite substances as implant materials have been directed to the improving the mechanical strength of the apatitie substances while maintaining the excellent affinity for a bone. For example, laid-open Japanese Patent Application (Kokai) No. 53-75209 discloses an implant material having a layer of flame sprayed apatite powder formed onto the periphery of a ceramic core. The flame sprayed layer of this implant material has a rough surface and the implant material can be firmly fixed to a bone by the anchor effect owing to the growth of the bone tissue in the rough area. Therefore, this implant material may provide an excellent artificial dental root, having mechanical strength improved by the reinforcement of the ceramic material and having good affinity for a bone.

However, in the practical use of artificial dental roots, it should be taken into consideration that it becomes necessary to extract the artificial dental root once implanted when any trouble has occurred. Thus, the above-mentioned implant material may not be suitable for practical use as an artificial dental root since it may have too high an affinity for a bone. In the implant denture technique, an artificial dental root is implanted into the jaw bone or the like and then, after two or three months, a denture is connected onto the implanted dental root. If trouble, such as the displacement or damage of the implanted root, the inflammation of the peripheral tissue or the like, occurs after the implantation of the root, it is necessary to immediately extract the implanted root. In such a case, if the artificial dental root has been extremely firmly fixed to a natural bone such as the jaw bone, a part of the bone may have to be resected to extract the implanted root, so that the patient may experience pain or the natural bone may be damaged.

SUMMARY OF THE INVENTION

The primary object of the present invention is to provide an artificial dental root which does not have the above-mentioned drawbacks.

Thus, according to the present invention, there is provided an artificial dental root comprised of a composition in which a particulate or powdered form of synthetic hydroxyapatite or calcined or sintered synthetic hydroxyapatite or a mixture thereof is dispersed in an organic matrix, the surface area of said synthetic dental root to be brought into contact with a bone being composed of both a phase of said hydroxyapatite and a phase of said organic matrix.

It has now been found that if a composite material obtained by molding a blend of a particulate or powdered form of hydroxyapatite of a specific particle diameter with an organic matrix has a specific area ratio of the hydroxyapatite phase to the organic matrix phase of the surface area to be brought into contact with a bone, the composite material has not only excellent mechanical properties but also moderate ability to coapt with a natural bone.

The term "moderate ability to coapt with a natural bone", as used herein, is intended to mean that the implanted artificial dental root is fixed to the natural bone with a moderate coaptation force which is sufficient to prevent the implanted root from being removed from the vital tissue in a normal state and to withstand the practical use of the resultant denture after the connection of the upper structure to the implanted root, but allows the extraction of the implanted root without damaging the natural bone when any problems may occur.

DESCRIPTION OF PREFERRED EMBODIMENTS

Hydroxyapatite usable for the present invention may be prepared by known processes. Thus, there may be employed synthetic hydroxyapatite prepared, for example, as described in Ceramics, 10, 7, 461(1975), by a dry process wherein $Ca_3(PO_4)_2$ is reacted with excessive $CaCO_3$ in a steam-containing air flow at a high temperature of 900 to 1300° C. or by a wet process wherein an aqueous solution of $Ca(NO_3)_2$ is reacted with an aqueous solution of $(NH_4)H_2PO_4$ under a $NH_4OH$ alkaline condition. There may also be employed sintered hydroxyapatite obtained by sintering the above-mentioned synthetic hydroxyapatite as well as sintered hydroxyapatite obtained by press molding synthetic hydroxyapatite prepared by a known process and sintering the molded product at 600 to 1500° C.

Hydroxyapatite can also be obtained from a natural bone, for example, by calcining a cattle bone at about 800° C. to remove the organic substances contained therein. However, where such hydroxyapatite is employed, there may arise problems with respect to the procurement of the starting material, uniformity in quality and the compatability to a living body or the bone formation speed owing to the presence of retained impurities.

The organic matrix should not deteriorate in a living body and should not deleteriously affect the vital tissue. Preferably, the organic matrix is comprised of one or more polymers selected from bisphenol A-glycidyl methacrylate polycondensates, polymethyl methacrylate, poly-2-hydroxyethyl methacrylate, polyethylene, polysulfones, polyamides, polyesters, polytetrafluoroethylene, polyvinylidene fluoride and polycarbonates, and copolymers of two or more monomers of said polymers.

The artificial dental root of the present invention may be prepared by blending a particulate or powdered from of hydroxyapatite as mentioned above with an organic matrix and molding the blend in a known manner. It is preferable that the hydroxyapatite has a particle diameter of not more than 1000 μm, particularly 100 to 0.01 μm. It is important that the hydroxyapatite phase is in a discontinous phase in the surface area of the resultant artificial dental root to be brought into contact with a bone. The area ratio of the hydroxyapatite phase to the organic matrix phase of the surface area to be brought into contact with a bone may preferably be 5:95 to 70:30, particularly 10:90 to 60:40. If the hydroxyapatite phase is in a continuous phase or occupies more than 70% of the surface area, the coaptation force of the resultant dental root with a natural bone may become too large so that the natural bone is damaged at the time of the extraction of the implanted dental root. On the other hand, if the hydroxyapatite phase occupies less than 5% of the surface area, the implanted dental root may be removed from the vital tissue in a normal state. It may be advantageous, from the stand point of durability and coaptability to the vital tissue, that the area ratio of the hydroxyapatite phase to the organic matrix phase be in a range from 10:90 to 60:40.

It will be appreciated from the above description that the characteristic feature of the present invention consists in the fact that the excellent ability of hydroxyapatite to coapt with a bone is advantageously controlled in the use of hydroxyapatite as material for an artificial dental root. Thus, the composite material described above with regard to the artificial dental root according to the present invention may not be suitable for use as a dental cement such as a sealant or filler for a bore or crack in a tooth, but is very useful for a practical artificial dental root.

The present invention will be further illustrated by the following non-limitative examples.

EXAMPLE 1

A mixture (pH 11 to 12) of 158.5 g (1.2 mols) of diammonium hydrogenphosphate, 3780 ml of distilled water and 1420 ml of concentrated ammonia was added dropwise to a stirred mixture of 328 g (2 mols) of calcium nitrate, 1320 ml of distilled water and 1180 ml of concentrated ammonia over the course of 30 minutes. The obtained suspension was centrifuged to obtain a cake. The cake was dried at 100° C. for 24 hours. Then, a part of the dried cake was heated at 500° C. for 3 hours in an electric furnace to obtain a hydroxyapatite powder and the remainder was sintered at 1250° C. for 60 minutes to obtain a white sintered hydroxyapatite.

The elementary analysis of the non-sintered and sintered hydroxyapatites proved that they had a Ca/P ratio of 1.66 and the X-ray diffraction thereof also proved that they were of high purity.

The hydroxyapatites obtained as mentioned above were ground and used as the starting material in the following examples.

EXAMPLE 2

A sintered hydroxyapatite powder having particle diameters of 10 to 70 μm was mixed with a bisphenol A-glycidyl methacrylate/methyl methacrylate mixture (weight ratio 6/4) at a volume ratio (calculated by specific gravity) of 1:1. After addition of 0.05% by weight of benzoyl peroxide as a polymerization initiator, the mixture was uniformly blended using a stirrer. Then, the blend was charged into a glass tube having an inner diameter of 5 mm and, after defoaming, subjected to a polymerization reaction at a temperature of 80° C. for 2 hours. Thus, a hydroxyapatite composition was obtained (Sample 1).

EXAMPLE 3

The procedure as described in Example 2 was repeated, except that a sintered hydroxyapatite having particle diameters of 100 to 500 μm was used and 2-hydroxyethyl methacrylate was used instead of methyl methacrylate. Thus, a hydroxyapatite composition was obtained (Sample 2).

EXAMPLE 4

By repeating the procedure as described in Example 2, except that a sintered hydroxyapatite and bisphenol A-glycidyl methacrylate/methyl methacrylate (weight ratio 6/4) were mixed at a volume ratio of 3:7, a hydroxyapatite composition was obtained (Sample 3).

EXAMPLE 5

A sintered hydroxyapatite powder having a mean particle diameter of 20 μm and a finely divided high-density polyethylene were uniformly blended at a volume ratio of 1:6 using a Henschel mixer, and the blend was press molded to obtain a hydroxyapatite composition (Sample 4).

EXAMPLE 6

A sintered hydroxyapatite powder having particle diameters of 30 to 70 μm and methyl methacrylate were mixed at a volume ratio of 1:1. Then, 0.05% by weight of benzoil peroxide was added as a polymerization initiator and the mixture was uniformly blended. The blend was defoamed in a glass tube having an inner diameter of 5 mm and heated at 80° C. for 2 hours to obtain a hydroxyapatite composition (Sample 5).

EXAMPLE 7

A sintered hydroxyapatite powder having of particle diameters of 30 to 70 μm was uniformly blended with a finely divided polysulfone or a finely divided polytetrafluoroethylene, respectively, at a volume ratio of 1:3, and the blend was press molded. Thus, hydroxyapatite compositions were obtained (Sample 6 and Sample 7, respectively).

EXAMPLE 8

A non-sintered hydroxyapatite powder having a mean particle diameter of 50 μm was uniformly blended with finely divided 6,6-nylon at a volume ratio of 1:3, and the blend was press molded to obtain a hydroxyapatite composition (Sample 8).

and a length of 10 mm, while the composition obtained in Example 11 was cut to a length of 10 mm. The cut samples were surgically implanted to a thighbone of an adult dog. After 6 months, the thighbone containing each sample was cut off and each thighbone piece was subjected to a test for evaluating the coaptation with a bone. The area ratios of the hydroxyapatite phase to the organic matrix phase of the respective samples determined before the implantation are shown in Table 1 below together with the results of the above-mentioned coaptation test and the results of an impact strength test.

The area ratios were evaluated from the photomicrographs of the surfaces of the respective samples. The coaptation test was carried out by placing each thighbone piece on the supporting plate of an Instron tester and slowly loading at a speed of 1 cm/min in the axial direction of the implanted sample.

TABLE 1

| Sample No. | | 1 | 2 | 3 | 4 | 5 | 6 | 7 | 8 | 9 | 10 | 11 | 12 |
|---|---|---|---|---|---|---|---|---|---|---|---|---|---|
| Area ratio of hydroxyapatite phase to organic matrix phase | | 50/50 | 50/50 | 30/70 | 14/86 | 50/50 | 25/75 | 25/75 | 25/75 | 3/97 | 75/25 | <1/99*** | <35/65 |
| Coaptation** | | | | | | | | | | | | | |
| (A) | Easiness to extract | 4/4 | 4/4 | 4/4 | 4/4 | 4/4 | 4/4 | 4/4 | 4/4 | * | 0/4 | * | 0/4 |
| (B) | Bone damage | 0/4 | 0/4 | 0/4 | 0/4 | 0/4 | 0/4 | 0/4 | 0/4 | * | 1/4 | * | 2/4 |
| (C) | Bone breading | 0/4 | 0/4 | 0/4 | 0/4 | 0/4 | 0/4 | 0/4 | 0/4 | * | 3/4 | * | 2/4 |
| Impact strength (ft.lb) | | 0.17 | 0.15 | 0.18 | 0.41 | 0.16 | 0.36 | 0.43 | 0.33 | 0.21 | 0.10 | 0.17 | 0.02 |

Note:
*The implanted sample was extracted by a very small load.
**Represented by the number of samples easily extracted/the total number of samples.
***The hydroxyapatite phase occupied less than 1% of the surface area.

EXAMPLE 9

(Comparison)

By repeating the procedure as described in Example 2, except that a sintered hydroxyapatite powder and bisphenol A-glycidyl methacrylate/methyl methacrylate (weight ratio 6/4) were mixed at a volume ratio of 3:97, a hydroxyapatite composition was obtained (Sample 9).

EXAMPLE 10

(Comparison)

By repeating the procedure in Example 2, except that a sintered hydroxyapatite powder and bisphenol A-glycidyl methacrylat /methyl methacrylate (weight ratio 6/4) was mixed at a volume ratio of 3:1, a hydroxyapatite composition was obtained (Sample 10).

EXAMPLE 11

(Comparison)

A hydroxyapatite composition (Sample 11) was prepared in the manner as in Example 2, except that a glass tube having an inner diameter of 4 mm was used.

EXAMPLE 12

(Comparison)

A sintered porous hydroxyapatite having a porosity of 65% was impregnated with a mixture of bisphenol A-glycidyl methacrylate/methyl methacrylate (weight ratio 6/4containing 0.05% by weight of benzoil peroxide under a reduced pressure. The impregnated hydroxyapatite was heated at 80° C. for 2 hours to obtain a hydroxyapatite composition (Sample 12).

The compositions obtained in Examples 2 through 10 and Example 12 were each cut to a diameter of 4 mm It is apparent from the above results that the artificial dental root of the present invention exhibits moderate affinity for bone and has high mechanical strength.

EXAMPLE 13

Sample 1 and Sample 9 were each cut into two columns having a diameter of 3.5 mm and a length of 10 mm. The columns were implanted into bores drilled in a jaw bone of an adult dog immediately after the extraction of teeth. The columns obtained from Sample 9 were both removed in a normal state after one month, while the columns obtained from Sample 1 were retained even after 6 months. One of the Sample 1 column was easily extracted by a usual tooth extraction technique without damaging the jaw bone. The jaw bone containing the other Sample 1 column was cut off after one year and subjected to observations by a light microscope and an X-ray photograph. It was proved that the implanted portion was cured and a new bone was formed in the gap between the implanted column and the jaw bone. Problems, such as inflamation, foreign-body reaction and the like were not at all observed.

What is claimed is:

1. A process for preparing an artificial dental root comprising uniformly blending a particulate or powdered form of synthetic hydroxyapatite or calcined or sintered synthetic hydroxyapatite or a mixture thereof with an organic matrix, molding the blend, cutting the surface of the molded product, and causing the cut surface area of the molded product to be brought into contact with a bone wherein said cut surface area is composed of both a phase of said hydroxyapatite and a phase of said organic matrix in a surface area ratio of hydroxyapatite phase to organic matrix phase of from 5:95 to 70:30.

2. Process of claim 1, wherein said ratio is about 10:90 to 60:40.

3. A process according to claim 1, wherein the particle diameter of said synthetic hydroxyapatite or calcined or sintered synthetic hydroxyapatite or said mixture is not more than 1000 μm.

4. A process according to claim 1, wherein one or more polymers selected from bisphenol A-glycidyl methacrylate polycondensates, polymethyl methacrylste, poly-2-hydroxyethyl methacrylate, polyethylene, polysulfones, polyamides, polyesters, polytetrafluoroethylene, polyvinylidene fluoride and polycarbonates, and copolymers of two or more monomers of said polymers are employed as said organic matrix.

* * * * *